US011293421B2

United States Patent
Sung et al.

(10) Patent No.: US 11,293,421 B2
(45) Date of Patent: Apr. 5, 2022

(54) APPARATUS FOR REDUCING SUCTION PULSATION AND SWASH PLATE TYPE COMPRESSOR COMPRISING SAME

(71) Applicant: Hanon Systems, Daejeon (KR)

(72) Inventors: Yeol Woo Sung, Daejeon (KR); Young Seop Yoon, Daejeon (KR)

(73) Assignee: Hanon Systems, Daejeon (KR)

( * ) Notice: Subject to any disclaimer, the term of this patent is extended or adjusted under 35 U.S.C. 154(b) by 448 days.

(21) Appl. No.: 16/327,408

(22) PCT Filed: Apr. 10, 2018

(86) PCT No.: PCT/KR2018/004196
§ 371 (c)(1),
(2) Date: Feb. 22, 2019

(87) PCT Pub. No.: WO2018/190616
PCT Pub. Date: Oct. 18, 2018

(65) Prior Publication Data
US 2019/0195211 A1    Jun. 27, 2019

(30) Foreign Application Priority Data

Apr. 11, 2017    (KR) ......................... 10-2017-0046781

(51) Int. Cl.
*F04B 39/00*    (2006.01)
*F04B 27/08*    (2006.01)
(Continued)

(52) U.S. Cl.
CPC .......... *F04B 39/0055* (2013.01); *F04B 25/04* (2013.01); *F04B 27/08* (2013.01);
(Continued)

(58) Field of Classification Search
CPC .. F04B 39/0055; F04B 39/00; F04B 39/0038; F04B 27/08; F04B 27/073; F04B 25/04; F16K 27/08
See application file for complete search history.

(56) References Cited

U.S. PATENT DOCUMENTS 4,542,852 A * 9/1985 Orth ........................ F25B 41/31
236/92 B
7,581,560 B2 * 9/2009 Koch ..................... F16K 15/026
137/543.19
(Continued)

FOREIGN PATENT DOCUMENTS

DE    102017116184 A1    1/2018
KR    10-2012-0072248 A    7/2012
(Continued)

*Primary Examiner* — Patrick C Williams
(74) *Attorney, Agent, or Firm* — Norton Rose Fulbright US LLP; James R. Crawford

(57) ABSTRACT

The present invention relates to an apparatus for reducing suction pulsation and a swash plate type compressor comprising same. The apparatus for reducing suction pulsation, which is installed in a swash plate type compressor and can reduce suction pulsation of a refrigerant, comprises: a case formed in a hollow container shape and having a suction port with an open upper side in the height direction and discharge openings formed by opened areas in the side wall thereof; a core portion formed inside the case, between the suction port and the discharge openings so as to be movable in the height direction; a lever having a vertical portion extending upwardly, along the side wall of the case, from one end of a horizontal portion disposed in the vicinity of the bottom wall of the case and coupled to the case such that the portion where the horizontal portion and the vertical portion meet is rotatable about a horizontal axis; and an elastic means interposed between the core portion and the horizontal portion of the lever.

18 Claims, 19 Drawing Sheets

(51) Int. Cl.
  *F16K 47/02* (2006.01)
  *F04B 25/04* (2006.01)

(52) U.S. Cl.
  CPC .......... *F04B 27/0873* (2013.01); *F04B 39/00* (2013.01); *F16K 47/02* (2013.01); *F04B 39/0038* (2013.01)

(56) References Cited

U.S. PATENT DOCUMENTS

| | | | |
|---|---|---|---|
| 8,757,199 B2* | 6/2014 | Chen | F16K 27/0236 137/505 |
| 9,004,099 B2* | 4/2015 | Kim | F16K 15/06 137/543.19 |
| 2011/0076171 A1 | 3/2011 | Park et al. | |

FOREIGN PATENT DOCUMENTS

| KR | 10-2013-0074496 A | 7/2013 |
|---|---|---|
| KR | 10-2013-0092876 A | 8/2013 |
| KR | 10-1607711 B1 | 3/2016 |
| KR | 10-2016-0097633 A | 8/2016 |

\* cited by examiner

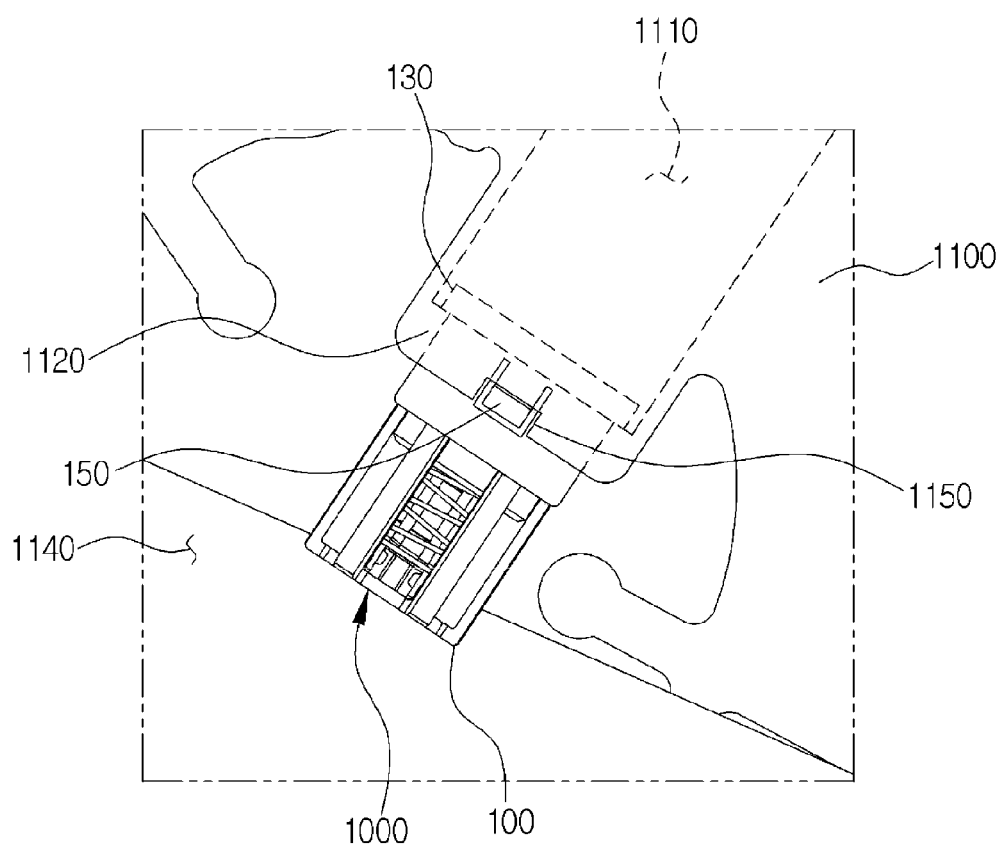

APPARATUS FOR REDUCING SUCTION PULSATION AND SWASH PLATE TYPE COMPRESSOR COMPRISING SAME

This patent application is a national phase under 35 U.S.C. § 371 of International Application No. PCT/KR2018/004196 filed Apr. 10, 2018, which claims priority from Korean Patent Application No. 10-2017-0046781, filed Apr. 11, 2017, each of which is hereby incorporated herein by reference in its entirety for all purposes.

TECHNICAL FIELD

The present invention relates to an apparatus for reducing suction pulsation installed on a suction flow passage formed in a rear housing of a swash plate type compressor to reduce the suction pulsation of a refrigerant, and a swash plate type compressor comprising the same.

BACKGROUND ART

A cooling system for a vehicle generally includes a compressor that serves to compress a refrigerant, and the compressor compresses the refrigerant by a reciprocating type in which the compressor performs compression while reciprocating and a rotary type in which the compressor performs compression while rotating.

In addition, various types of compressors exist, and as the compressor, a variable displacement swash plate type compressor which is driven by receiving power from a rotational force of an engine and is capable of changing an inclination angle of a swash plate while being always driven along with driving of the engine of a vehicle without an electromagnetic clutch is widely used. In such a variable displacement swash plate type compressor, a pressure control valve for adjusting the inclination angle of the swash plate is generally used for adjusting a discharge amount of the refrigerant.

However, the conventional variable displacement swash plate type compressor has a problem that when a suction amount of the refrigerant is reduced, vibration occurs in a suction port, which may cause pulsation or noise.

In order to solve the above-mentioned problem, Korean Patent No. 10-1607711 (registered on Mar. 24, 2016 titled "variable capacity swash plate compressor"), which is the technology related to an apparatus for reducing suction pulsation for preventing a rapid suction by slowly changing a flow area of the suction port when the suction amount of the refrigerant is small, has been disclosed, and a suction check valve 10 as illustrated in FIG. 1 is suggested.

Such a suction valve 10 includes a case 20, an opening and closing core 30, and an elastic spring 40, and the case 20 includes an opened suction port 21 made of a metal material and formed in an upper end thereof, and a discharging port 22 formed in one side of a side wall thereof while being perpendicular to the suction port 21. In addition, the opening and closing core 30 is a cylindrical plunger which is installed in the case 20 to be movable in an axial direction, and serves to intermit the flow of the refrigerant from the suction port 21 to the discharging port 22 while moving up and down the inside of the case 20 according to pressure of the refrigerant applied to the suction port 21. The elastic spring 40 is installed to elastically support the opening and closing core 30 against the pressure of the refrigerant introduced into the case 20 through the suction port 21, and allows the opening and closing core 30 to be in close contact with the suction port 21 when the pressure of the refrigerant is not applied to the suction port 21 to thereby close the suction port 21. In addition, a small amount of refrigerant may flow through an axial groove 31 even in a state in which the opening and closing core 30 is in close contact with the suction port 21 by the axial groove 31 formed in an outer circumferential surface of the opening and closing core 30, and as a result, even though the pressure of the refrigerant applied to the suction port 21 is sharply changed, a sharp change in an opening degree of the suction check valve may be prevented.

However, the conventional suction check valve as described above has an inner circumferential surface of the case 20 and the outer circumferential surface of the opening and closing core 30 slightly spaced apart from each other so that the opening and closing core 30 may be smoothly moved up and down, and there is a problem that the opening and closing core 30 is shaken by the refrigerant passing between the case 20 and the opening and closing core 30 and collides with the side wall of the case 20, which causes vibration and noise. In addition, there is a problem that a manufacturing cost of the suction check valve is increased due to the suction port 21 made of the metal material to press-fix the suction check valve into the suction flow passage of the housing.

RELATED ART DOCUMENT

Patent Document

KR 10-1607711 B1 (2016 Mar. 24)

DISCLOSURE

Technical Problem

An object of the present invention is to provide an apparatus for reducing suction pulsation installed on a suction flow passage formed in a rear housing of a swash plate type compressor to reduce the suction pulsation of a refrigerant and to prevent an occurrence of vibration and noise, and a swash plate type compressor comprising the same.

An object of the present invention is to provide an apparatus for reducing suction pulsation in which a manufacturing cost is inexpensive because all the configurations except an elastic spring are made of plastic, and in particular, a conventional suction port made of metal is replaced with the plastic and is integrally manufactured with a case, and a swash plate type compressor comprising the same.

Technical Solution

In one general aspect, an apparatus reducing suction pulsation includes: a case 100 having a suction port 110 having an upper side surface opened in a height direction and a discharging port 120 formed by hollowing a predetermined region of a side wall 102; a core part 200 provided between the suction port 110 and the discharging port 120 in the case 100 to be movable in the height direction, and disposed to be spaced apart from a bottom surface of the case 100; a lever 300 in which a vertical part 320 extends upwardly along the side wall 102 of the case 100 at one end of a horizontal part 310 disposed in the vicinity of the bottom wall 101 of the case 100 to dispose an upper side of the vertical part 320 close to an outer circumferential surface of the core part 200, and a portion at which the horizontal part 310 and the vertical part 320 meet is rotatably coupled to the case 100 about a horizontal shaft; and an elastic means 400 interposed between the core part 200 and the horizontal part 310 of the lever 300 and having an upper end supported by the core part 200 and a lower end supported by the horizontal part 310.

The case 100 and the lever 300 may be integrally formed of a plastic material by injection.

The lever 300 may be disposed in an opening 121 formed in the bottom wall 101 and the side wall 102 so as to penetrate through an inner side and an outer side of the case 100.

Protrusions 122 may protrude toward the lever 300 so as to be close to the lever 300 on a circumferential surface forming the opening 121.

An upper surface of the horizontal part 310 of the lever 300 may be positioned above an upper surface of the bottom wall 101 of the case 100, and a lower end of the elastic means 400 may be supported by the horizontal part 310, and both sides of the lower end of the elastic means 400 in the horizontal direction may be disposed to be spaced apart from an upper side of the bottom wall 101.

A core hook part 140 may protrude in an inner diameter direction on a predetermined region of an inner circumferential surface of the case 100 so that the core part 200 may be caught on the core hook part 140 in a state in which the core part 200 is inserted into the case 100 and does not escape upwardly.

A hook moving groove 210 may be formed in the outer circumferential surface of the core part 200 at a position corresponding to the core hook part 140 so as to be concave from the upper end of the core part 200 to a height spaced apart upwardly from the lower end thereof, and the core hook part 140 may be inserted into the hook moving groove 210.

Slits 141 cut in the height direction at both ends in the circumferential direction in which the core hook part 140 is formed may be formed in the case 100.

The core part 200 may have a plurality of blocking walls 220 extended upwardly from the upper surface of the core part 200 of positions corresponding to positions at which the slits 141 are formed.

Stoppers 230 may protrude in the outer diameter direction on a predetermined region of the outer circumferential surface of the core part 200, and the stoppers 230 may be caught on an upper end of the opening formed to penetrate through the side wall 102 of the case 100 in a state in which the core part 200 is inserted into the case 100 to prevent the core part 200 from escaping upwardly.

The case 100 may have a first catching part 130 formed to protrude in the outer diameter direction on the upper end of the outer circumferential surface thereof, and a second catching part 150 formed to protrude in the outer diameter direction on the outer circumferential surface of the case 100 at a position spaced apart downwardly from the first catching part 130.

The case 100 may have a catching protrusion 161 protruding in the outer diameter direction from an upper end of an extending part 160 extended upwardly in the height direction from the upper end of the case 100.

The apparatus for reducing suction pulsation may further include: a fixing member 500 in which a plurality of extending parts 520 are extended downwardly from a ring part 510 to be spaced apart from each other in a circumferential direction so that coupling protrusions 521 protrude in the outer diameter direction from lower ends of the plurality of extending parts 520, and a plurality of extending parts 530 are extended upwardly from the ring part 510 to be spaced apart from each other in the circumferential direction so that catching protrusions 531 protrude in the outer diameter direction from upper ends of the plurality of extending parts 530, wherein the case 100 has coupling grooves 170 formed therein so that the catching protrusions 531 of the fixing member 500 are inserted and fixed to the coupling grooves 170 of the case 100.

The case 100 may have a limiter 180 protruding inwardly from the bottom wall 101 or the side wall 102 to limit a range in which the core part 200 is moved downwardly.

In another general aspect, a swash plate type compressor includes: a rear housing 1100 in which a suction flow passage 1110 through which a refrigerant is introduced; and the apparatus 1000 for reducing suction pulsation insertedly installed on the suction flow passage of the rear housing 1100.

A catching jaw 1120 may protrude inwardly from the suction flow passage 1110 of the rear housing 1100, the case 100 may have a first catching part 130 protruding in the outer diameter direction from the upper end of the outer circumferential surface thereof, and a second catching part 150 protruding in the outer diameter direction from the outer circumferential surface of the case 100 at a position spaced apart downwardly from the first catching part 130, and the catching jaw 1120 of the rear housing 1100 may be caught and sandwiched between the first catching part 130 and the second catching part 150 of the case 100.

A catching groove 1130 may be formed to be concave in the suction flow passage 1110 of the rear housing 1100, the case 100 may have catching protrusion 161 protruding in the outer diameter direction from an upper end of an extending part 160 extended upwardly in the height direction from the upper end of the case 100, and the catching protrusion 161 of the case 100 may be inserted and coupled to the catching groove 1130 of the rear housing 1100.

A catching groove 1130 may be formed to be concave in the suction flow passage 1110 of the rear housing 1100, and the apparatus 1000 for reducing suction pulsation may further include a fixing member 500 in which a plurality of extending parts 520 are extended downwardly from a ring part 510 to be spaced apart from each other in a circumferential direction so that coupling protrusions 521 protrude in the outer diameter direction from lower ends of the plurality of extending parts 520, and a plurality of extending parts 530 are extended upwardly from the ring part 510 to be spaced apart from each other in the circumferential direction so that catching protrusions 531 protrude in the outer diameter direction from upper ends of the plurality of extending parts 530, wherein the case 100 has coupling grooves 170 formed therein so that the catching protrusions 521 of the fixing member 500 are inserted and fixed to the coupling grooves 170 of the case 100, and the catching protrusions 531 of the case 100 are inserted and coupled to the catching groove 1130 of the rear housing 1100.

Advantageous Effects

The apparatus for reducing suction pulsation and the swash plate type compressor comprising the same may reduce the suction pulsation when the suction amount of the refrigerant is reduced, and prevent the occurrence of the vibration and the noise.

In addition, since all the configurations of the apparatus for reducing suction pulsation except for the elastic means are manufactured with the plastic, and in particular, the conventional suction port made of the metal is replaced with the plastic and is manufactured integrally with the case, the apparatus for reducing suction pulsation may be manufactured at the low cost.

DESCRIPTION OF DRAWINGS

FIG. 19 is a schematic view illustrating another example of the rear housing of the swash plate type compressor according to the present invention.

BEST MODE

Hereinafter, an apparatus for reducing suction pulsation and a swash plate type compressor comprising the same according to the present invention having the configurations as described above will be described in detail with reference to the accompanying drawings.

First, a structure of a swash plate type compressor will be briefly described. The swash plate type compressor is configured to generally include a housing, a rotary shaft, a swash plate, and a plurality of pistons.

The housing, which is a part forming an outer body of the swash plate type compressor, is formed therein with a cylinder chamber accommodating the rotary shaft, the swash plate, and the plurality of pistons, and a suction flow passage 1110 for supplying a refrigerant to the cylinder chamber during a suction stroke of the piston and a discharging flow passage through which the refrigerant in the cylinder chamber is discharged during a compression stroke of the piston are formed in a rear housing 1100 of the housing.

The rotary shaft is a means for transmitting a rotational driving force of an external driving source to the inside of the compressor, and the swash plate is a means for converting the rotational driving force of the rotary shaft into a reciprocating linear motion of the piston and is mounted on the rotary shaft in an inclined state so as to be rotated together with the rotary shaft.

The plurality of pistons are means for compressing the refrigerant while reciprocating inside the cylinder chamber by the swash plate and discharge the refrigerant sucked into the cylinder chamber through the suction flow passage 1110 to an external refrigerant line through the discharging flow passage.

In particular, a variable displacement swash plate type compressor is installed so that an inclination angle of the swash plate varies, and when an inclination of the swash plate with respect to the rotary shaft is 90 degrees, the reciprocating motion of the piston disappears, so that the rotary shaft idles. On the contrary, when the swash plate is tilted so as to be inclined at a specific angle other than 90 degrees with respect to the rotary shaft, the piston sucks the refrigerant while reciprocating in the cylinder chamber, compresses the refrigerant, and discharges the compressed refrigerant.

Here, a suction port through which the refrigerant is introduced from the outside is formed at a front end of the suction flow passage 1110, and the apparatus 1000 for reducing suction pulsation according to the present invention is mounted on the suction flow passage 1110 so that the suction pulsation may be reduced while a core part 200 moves according to suction pressure.

Exemplary Embodiment 1 and Exemplary Embodiment 2

Figure 7:
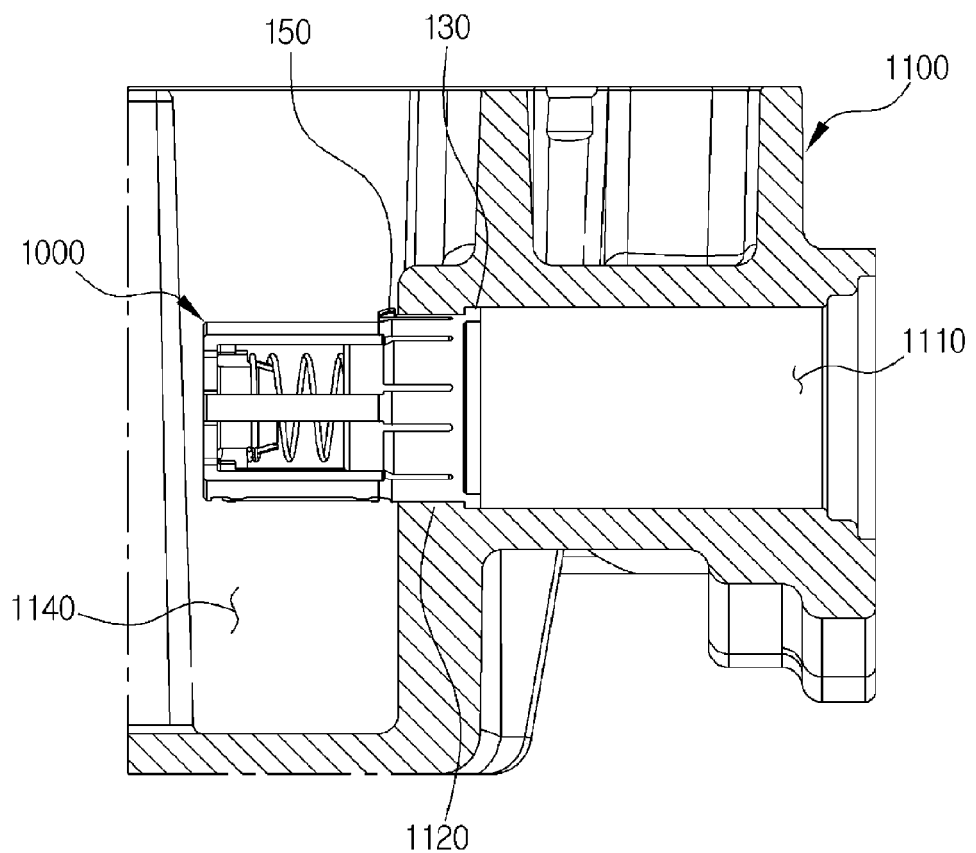
FIG. 7 is a cross-sectional view illustrating a portion of a rear housing of a swash plate type compressor on which the apparatus for reducing suction pulsation according to the first exemplary embodiment of the present invention is installed.
Figure 8:
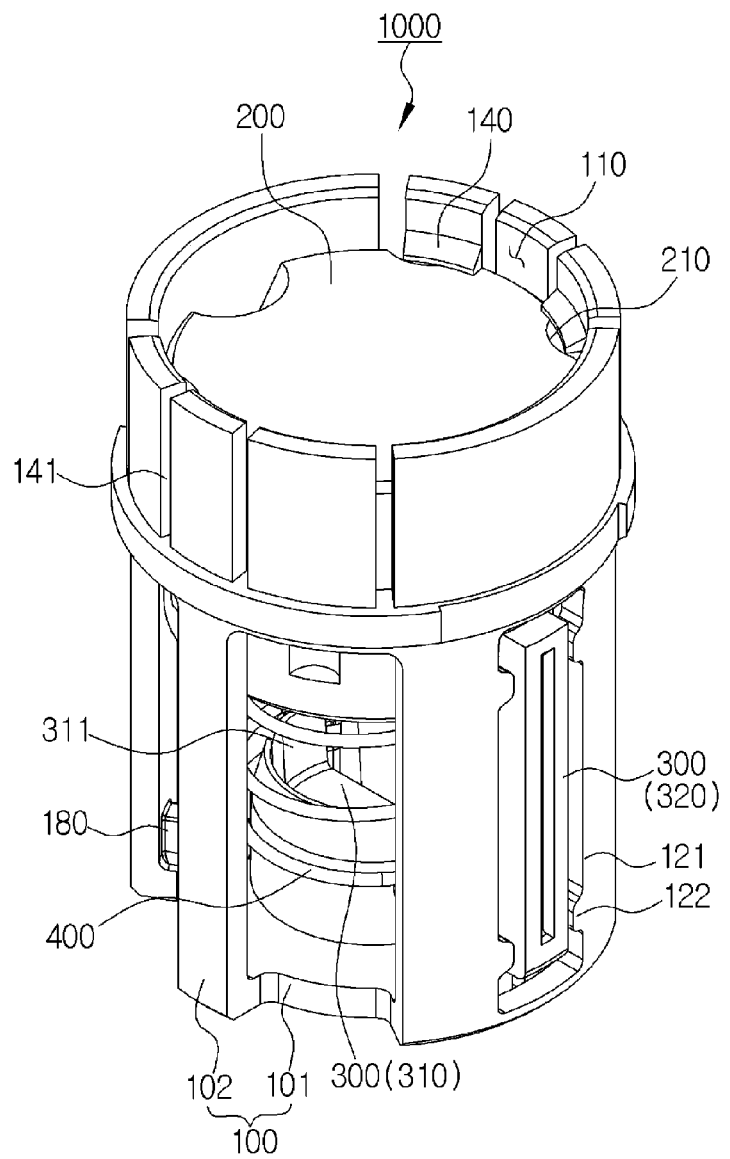
FIGS. 8 and 9 are an assembled perspective view illustrating an apparatus for reducing suction pulsation, and an upper plan view illustrating a case and a lever according to a second exemplary embodiment of the present invention.
Figure 9:
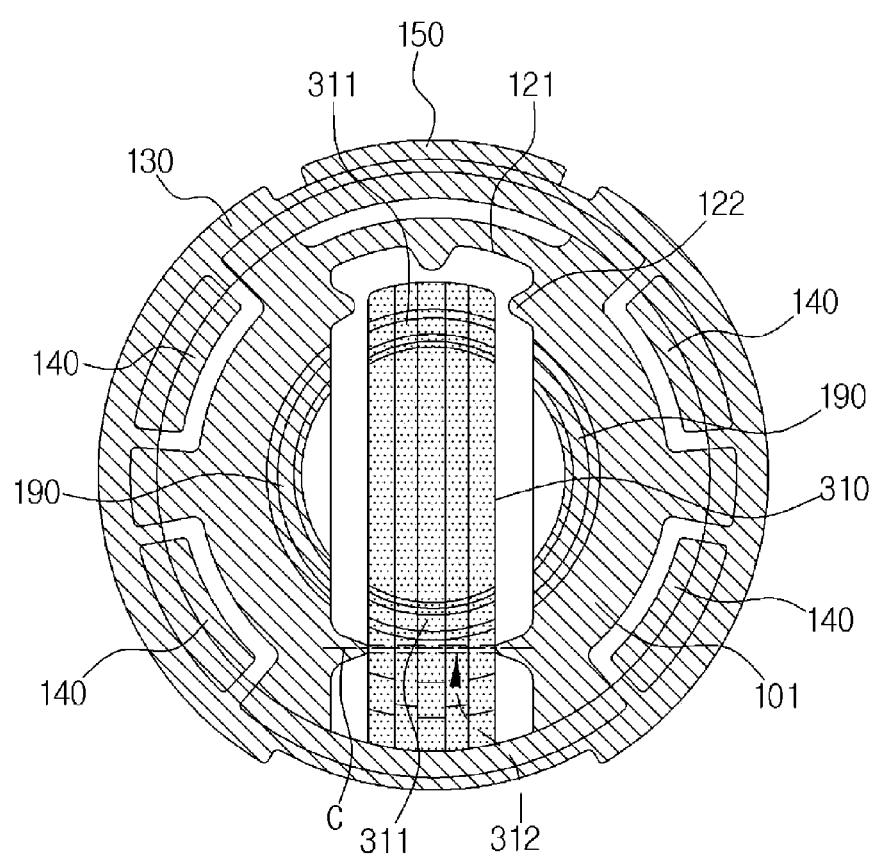

FIGS. 2 to 6 are an exploded perspective view, an assembled perspective view, and a cross-sectional view illustrating an apparatus for reducing suction pulsation according to a first exemplary embodiment of the present invention, and FIG. 7 is a cross-sectional view illustrating a portion of a rear housing of a swash plate type compressor on which the apparatus for reducing suction pulsation according to the first exemplary embodiment of the present invention is installed. FIGS. 8 and 9 are an assembled perspective view illustrating an apparatus for reducing suction pulsation, and an upper plan view illustrating a case and a lever according to a second exemplary embodiment of the present invention.

As illustrated, the apparatus 1000 for reducing suction pulsation according to the present invention may be configured to include a case 100 having a suction port 110 having an upper side surface opened in a height direction and a discharging port 120 formed by hollowing a predetermined region of a side wall 102; a core part 200 provided between the suction port 110 and the discharging port 120 in the case 100 to be movable in the height direction, and disposed to be spaced apart from a bottom surface of the case 100; a lever 300 in which a vertical part 320 extends upwardly along the side wall 102 of the case 100 at one end of a horizontal part 310 disposed in the vicinity of the bottom wall 101 of the case 100 to dispose an upper side of the vertical part 320 close to an outer circumferential surface of the core part 200, and a portion at which the horizontal part 310 and the vertical part 320 meet is rotatably coupled to the case 100 about a horizontal shaft; and an elastic means 400 interposed between the core part 200 and the horizontal part 310 of the lever 300 and having an upper end supported by the core part 200 and a lower end supported by the horizontal part 310.

First, the apparatus 1000 for reducing suction pulsation according to the present invention may be configured to generally include the case 100, the core part 200, the lever 300, and the elastic means 400.

The case 100 may be formed in a substantially cylindrical shape, and one end of the cylindrical shape may be opened and the other end thereof may be partially closed. That is, the case 100 may be formed in a shape of a concave container in which the side wall 102 thereof is formed in the cylindrical shape and a lower end of the side wall 102, which is a lower side in the height direction, is closed with the bottom wall 101. In addition, an opened upper end of the case 100 may be formed as the suction port 110, and the discharging port 120 in which a predetermined region of the side wall 102 is hollowed so as to penetrate through an outer circumferential surface and an inner circumferential surface may be formed. That is, a portion in which the side wall 102 is partially opened may be the discharging port 120. Here, a plurality of discharging ports 120 may be formed to be spaced apart from each other along a circumferential direction of the side wall 102.

The core part 200 moves in the height direction inside the case 100 according to a suction pressure of the refrigerant which is introduced from the suction port 110 to adjust an opening and closing area of the discharging port 120. That is, the core part 200, which is a means for intermitting a flow of the refrigerant passing through the inside of the case 100, moves in the height direction according to the pressure of the refrigerant which is introduced through the suction port 110 of the case 100, and the opening degree of the discharging port 120, which is a flow cross sectional area, which the refrigerant introduced through the suction port 110 may pass through the inside of the case 100 and may be discharged to the discharging port 120 may be adjusted according to a height of the core part 200. In addition, the core part 200 may be formed in a cylindrical shape corresponding to an inside shape of the case 100 so as to be movable along the height direction inside the case 100, and as an example, the core part 200 may be formed in the shape of a container formed to be upwardly concave from a lower surface thereof, as illustrated.

Here, the core part 200 may have an outer diameter slightly smaller than an inner diameter of the side wall 102 of the case 100 so that the core portion 200 is provided inside the case 100 to be smoothly moved up and down along the height direction. In addition, the core part 200 may be disposed between the suction port 110 and the discharging port 120, and the core part 200 may be disposed at a position spaced apart upwardly from the bottom wall 101 of the case 100.

As an example, as illustrated, the lever 300 may have a horizontal part 310 formed in a shape of "L" and formed in a horizontal direction perpendicular to the height direction, and a vertical part 320 extended upwardly from one end of the horizontal part 310 in the height direction. In addition, the horizontal part 310 may be disposed in the vicinity of the bottom wall 101 of the case 100 so as to be spaced apart downwardly from the core part 200, and the vertical part 310 may be disposed in the vicinity of the side wall 102 so that an upper side of the vertical part 310 may be disposed close to the outer circumferential surface of the core part 200. In addition, a part of a corner portion of the lever 300 of the form of "L", which is the portion at which the horizontal part 310 and the vertical part 320 meet and are connected to each other, is coupled to the case 100, and the lever 300 may be formed to be rotatable about the horizontal shaft C in a state in which the case 100 is fixed (see FIG. 9). In this case, as illustrated, a coupling part 312 may be formed in the form in which the lower side of the horizontal part 310 is coupled to a local portion of the bottom wall 101 at a corner portion at which the horizontal part 310 and the vertical part 320 of the lever 300 meet and are connected to each other, and the coupling part 312 may be folded or bent so that the lever 300 may be rotated with respect to the coupling part 312. A portion of the formed coupling part 312 that supports the lever 300 may have the form in which both ends of a flat plate portion standing in the height direction in the opening 121 formed to penetrate upper and lower surfaces of the bottom wall 101 are coupled to an edge of the opening 121. In addition, the coupling part 312 may be formed in various forms in which the lever 300 may be rotated about the horizontal shaft C.

The elastic means 400 may be, for example, a coil spring, and the elastic means 400 may be interposed between the core part 200 and the horizontal part 310 of the lever 300 and have an upper end supported by the core part 200 and a lower end supported by an upper surface of the horizontal part 310. In this case, an upper portion of the elastic means 400 may be inserted and coupled to an empty interior of the core part 200, and a lower portion of the elastic means 400 may be fitted and coupled to an outer side of a fitting part 311 protruding upwardly from the upper surface of the horizontal portion 310 of the lever 300. In addition, the lower portion of the elastic means 400 may also be fitted and coupled to a fitting part 190 of the case 100 formed on the same circumference as the fitting part 311 of the lever 300.

As a result, when a force greater than elasticity of the elastic means 400 is applied to the core part 200 due to the pressure of the refrigerant at the upper side of the core part 200 which is the suction port 110 side of the case 100, the horizontal part 310 of the lever 300 is pressed downwardly by the force of the elastic means 400 while the core part 200 is moved downwardly, and therefore, the upper portion of the vertical part 320 of the lever 300 rotated while the lever 300 rotates slightly about the horizontal axis C pushes the core part 200 to one side, such that the core part 200 may be maintained in a state in which it is in close contact with one side of the inner circumferential surface of the side wall 102 of the case 100. In this case, since the core part 200 moves up and down in the height direction according to the pressure of the refrigerant in the state in which it is in close contact with the inner circumferential surface of the side wall 102, the core part 200 does not vibrate in the horizontal direction even though the refrigerant flows from the suction port 110 of the case 100 to the discharging port 120, thereby making it possible to prevent vibration and noise generated when the core part 200 collides the side wall 102. In addition, since the upper portion of the vertical part 320 of the lever 300 is always operated to closely contact the core part 200 to one side of the inner circumferential surface of the side wall 102 in a state in which the elastic means 400 is compressed, the vibration of the core part 200 may be prevented simultaneously with the start of movement of the core part 200.

In addition, the case 100 and the lever 300 may be integrally formed of a plastic material by injection.

That is, the case 100 and the lever 300 may be integrally formed by the injection molding using the plastic material, and as a result, a configuration of the coupling part 312, which is a portion that the case 100 and the lever 300 are coupled to each other, may be easily formed, the configuration of the coupling part 312 may be easily manufactured, and a manufacturing cost thereof may be reduced. In this case, when the case 100 and the lever 300 are integrally manufactured by injection using a material that is unbreakable and may not cause fatigue fracture even in a repetitive bending load, breakage of the coupling part 312 may be prevented even though the lever 300 repeatedly rotates. Alternatively, the case 100 and the lever 300 may be formed as separate parts and may be coupled to each other by assembling.

In addition, the lever 300 may be disposed in the opening 121 formed in the bottom wall 101 and the side wall 102 so as to penetrate through an inner side and an outer side of the case 100.

That is, as illustrated, the lever 300 may be disposed the opening 121 formed to penetrate through the upper and lower surfaces of the bottom wall 101 of the case 100 and the opening 121 formed to penetrate through the inner and outer circumferential surfaces of the side wall 102, and the lever 300 may be disposed to be spaced apart from a circumferential surface of the opening 121. As a result, the lever 300 may be formed in a shape that the lever 300 closes most of the opening 121.

In addition, protrusions 122 may protrude toward the lever 300 so as to be close to the lever 300 on the circumferential surface forming the opening 121.

That is, the protrusions 122 protrude toward the lever 300 in a portion of the circumferential surface forming the opening 121 so as to be close to the lever 300 so that other movements other than the rotation about the horizontal shaft C of the lever 300 may be reduced.

In addition, the upper surface of the horizontal part 310 of the lever 300 may be positioned above the upper surface of the bottom wall 101 of the case 100, and the lower end of the elastic means 400 may be supported by the horizontal part 310, and both sides of the lower end of the elastic means 400 in the horizontal direction may be disposed to be spaced apart from the upper side of the bottom wall 101.

That is, the upper surface of the horizontal part 310 of the lever 300 is formed at a position higher than the upper surface of the bottom wall 101 of the case 100 so that the lower end of the elastic means 400 may be supported only by the horizontal part 310 of the lever 300, and the horizontal part 310 of the lever 300 is formed so that both side portions of the lower end of the elastic means 400 float in the horizontal direction of the shaft C in the horizontal part 310, and both sides of the lower end of the elastic means 400 may be positioned at positions spaced apart upwardly from the bottom wall 101. As a result, when the core part 200 is moved downwardly, the elastic means 400 downwardly pushes the horizontal part 310 to move the elastic means 400 together while the lever 300 rotates, and the lever 300 may not be rotated any more when the lower end of the elastic means 400 is supported by the bottom wall 101, and accordingly, the upper side of the vertical part 320 of the lever 300 may be prevented from pushing the core part 200 with a force greater than a specific force. Accordingly, the core part 200 may be maintained in close contact with the inner circumferential surface of the side wall 102 with an appropriate force so that the core part 200 may be smoothly moved up and down in the case 100 according to the pressure of the refrigerant.

In addition, a core hook part 140 protrudes in an inner diameter direction on a predetermined region of the inner circumferential surface of the case 100 so that the core part 200 is caught on the core hook part 140 in a state in which the core part 200 is inserted into the case 100 and does not escape upwardly.

That is, since the core part 200 may escape upwardly through the suction port 110 when a force due to a suction pressure of the refrigerant is smaller than the elastic force of the elastic means 400, a means capable of supporting the core part 200 in a direction opposite to the elastic force of the elastic means 400 is required. Accordingly, the core hook part 140 protruding in the inner diameter direction is formed on the predetermined region of the inner circumferential surface of the case 100 so that the core part 200 is caught on the core hook part 140 and does not escape upwardly.

In addition, a hook moving groove 210 is formed in the outer circumferential surface of the core part 200 at a position corresponding to the core hook part 140 so as to be concave from the upper end of the core part 200 to a height spaced apart upwardly from the lower end thereof, and the core hook part 140 may be inserted into the hook moving groove 210.

That is, the hook moving groove 210 may be formed to be concave in the outer circumferential surface of the core part 200 in the inner diameter direction, and the hook moving groove 210 is formed downwardly from the upper surface of the core part 200 and is formed only up to the height spaced apart upwardly from the lower surface of the core part 200 so that the core part 200 may be moved in the height direction in the state in which the core hook part 140 is inserted into the hook moving groove 210, and a lower end of the hook moving groove 210 in the height direction may be caught on the core hook part 140. As a result, the core part 200 may not be rotated with respect to the center shaft in the height direction, and it is possible to prevent the core part 200 from being released to the outside of the case 100. In addition, a guide groove 240 is formed in the outer circumferential surface of the core part 200 to be concave from the upper surface thereof to the lower surface thereof so that a portion of the vertical part 320 of the lever 300 may be inserted into the guide groove 240. As a result, it is possible to prevent the core part 200 from being rotated, and it is possible to allow the vertical part 320 of the lever 300 to accurately push the core portion 200.

In addition, slits 141 cut in the height direction at both ends in the circumferential direction in which the core hook part 140 is formed may be formed in the case 100.

That is, since the slits 141 are formed on both sides of the core hook part 140 along the height direction upwardly or downwardly, the portion in which the core hook part 140 is formed is pushed in an outer diameter direction by the core part 200 when the core part 200 is inserted into and assembled to the case 100 and the core part 200 may be easily inserted into the case 100, and after the core part 200 is inserted into the case 100, the core part 200 may be restored to its original shape by elasticity and the core part 200 may be caught on the core hook part 140 so as not to escape in a direction opposite to the inserted direction. In this case, as illustrated in FIGS. 2 to 6, the core hook part 200 may also be formed in the inner diameter direction at a lower end of a portion extended downwardly from the upper end of the side wall of the case 100, and as illustrated in FIGS. 8 and 9 illustrating the second exemplary embodiment of the apparatus 1000 for reducing suction pulsation according to the present invention, the core hook part 200 may also be formed in the inner diameter direction at a portion extended upwardly from the upper end of the side wall of the case 100.

Third Exemplary Embodiment

Figure 10:
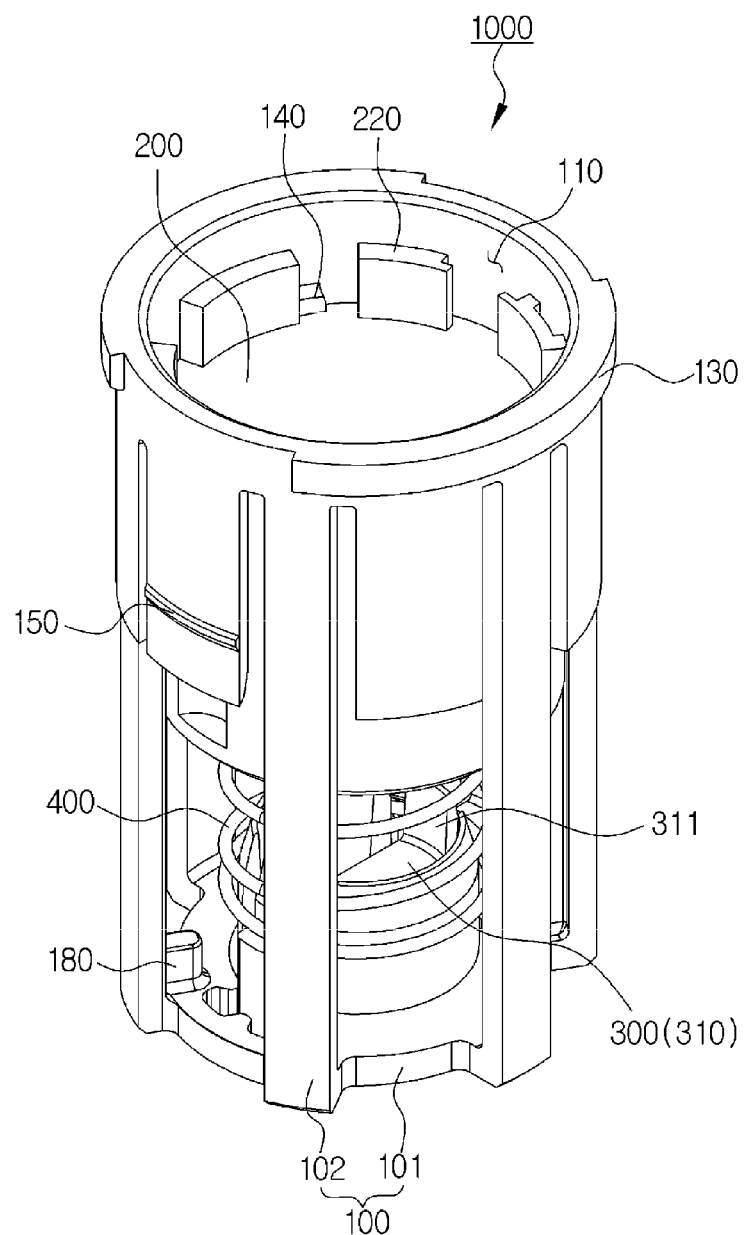
FIGS. 10 and 11 are an assembled perspective view illustrating an apparatus for reducing suction pulsation, and a perspective view illustrating a core part according to a third exemplary embodiment of the present invention.
Figure 11:
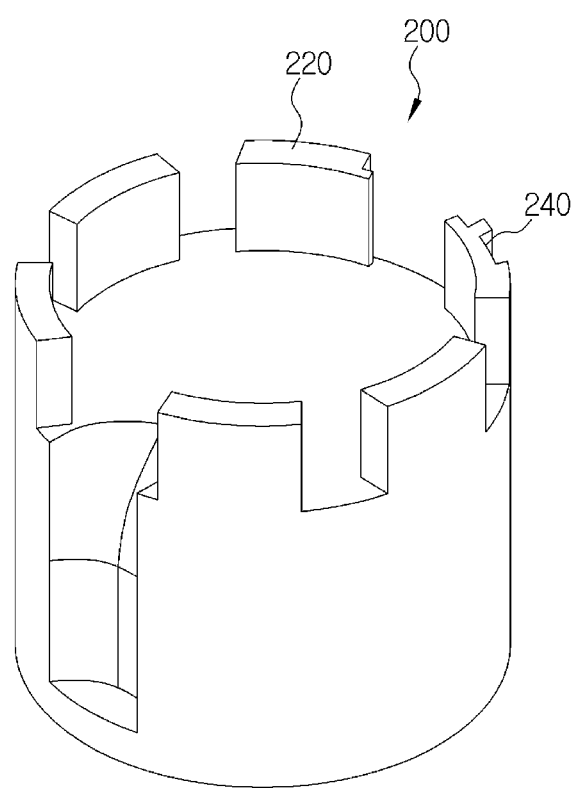

FIGS. 10 and 11 are an assembled perspective view illustrating an apparatus for reducing suction pulsation, and a perspective view illustrating a core part according to a third exemplary embodiment of the present invention.

As illustrated, the core part 200 may have a plurality of blocking walls 220 extended upwardly from the upper surface of the core part 200 of positions corresponding to the positions at which the slits 141 are formed.

That is, in the case in which the slits 141 are formed in the side wall 102 in the height direction as described above, since the refrigerant may flow through the slits 141 as well as the discharging port 120 when the core part 200 moves downwardly, the plurality of blocking walls 220 may be formed upwardly from the upper surface of the core part 200 so as to block the slits 141. In this case, the blocking walls 220 may be formed at the positions corresponding to the positions of the slits 141 when viewed from the top, and the blocking walls 220 may be formed in a region wider than a region in the circumferential direction in which the slits 141 are formed, thereby preventing the refrigerant from passing through the slits 141. In addition, lengths of the slits 141 in the height direction and lengths of the blocking walls 220 in the height direction may be adjusted to prevent the refrigerant from flowing through the slits 141 or allow some refrigerant to pass through the slits 141.

Fourth Exemplary Embodiment

Figure 12:
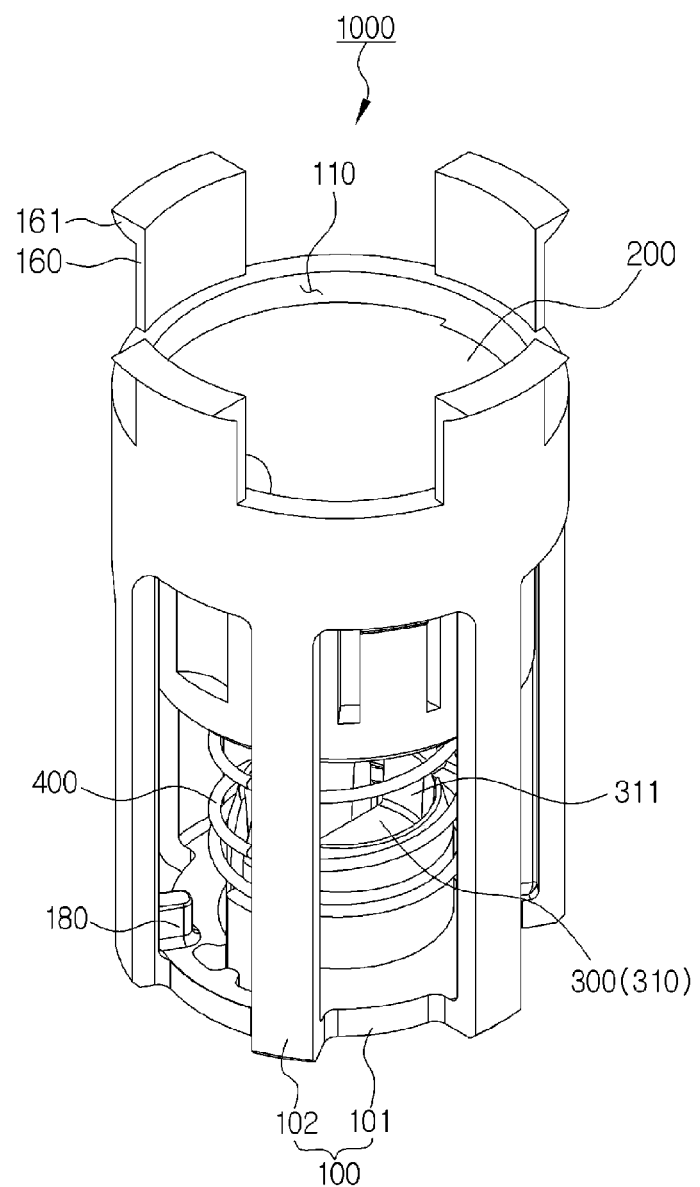
FIGS. 12 to 14 are an assembled perspective view illustrating an apparatus for reducing suction pulsation, a perspective view illustrating a core part, and a cross-sectional view illustrating the apparatus for reducing suction pulsation according to a fourth exemplary embodiment of the present invention.
Figure 13:
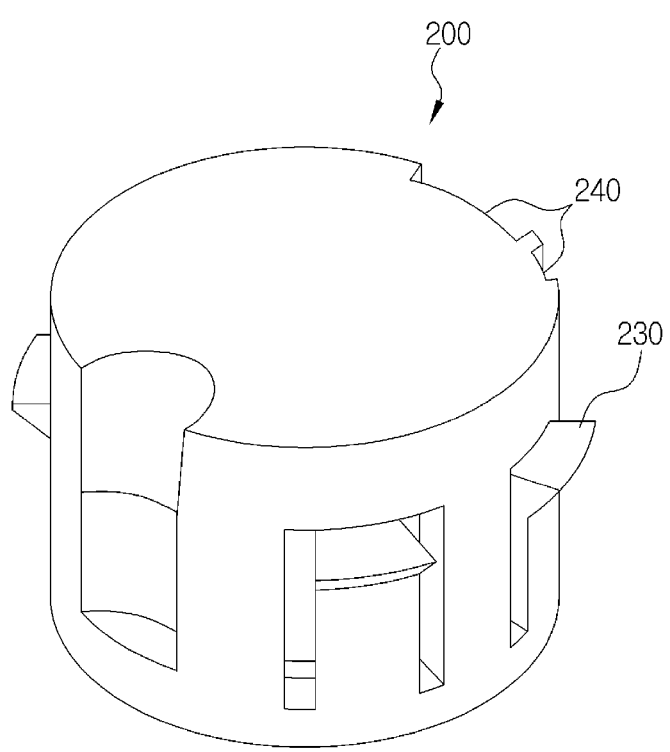
Figure 14:
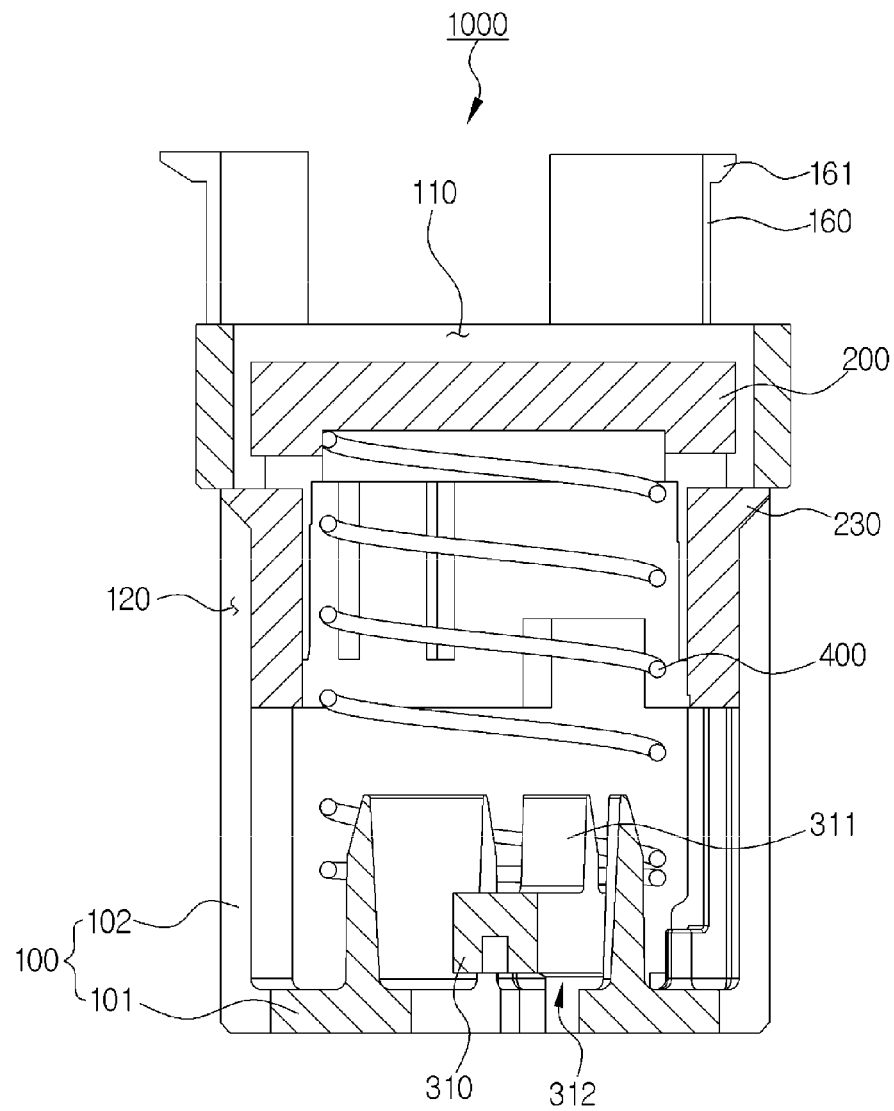

FIGS. 12 to 14 are an assembled perspective view illustrating an apparatus for reducing suction pulsation, a perspective view illustrating a core part, and a cross-sectional view illustrating the apparatus for reducing suction pulsation according to a fourth exemplary embodiment of the present invention.

As illustrated, stoppers 230 protrude in the outer diameter direction on a predetermined region of the outer circumferential surface of the core part 200 so that the stoppers 230 may be caught on the upper end of the opening formed to penetrate through the side wall 102 of the case 100 in the state in which the core part 200 is inserted into the case 100 to thereby prevent the core part 200 from escaping upwardly.

That is, a limit that the core part 200 may be moved upwardly by being caught on the case 100 may be determined so that the core part 200 does not escape to the outside of the case 100 in the state in which the core part 200 inserted into the case 100. In this case, the stoppers 230 may protrude in the outer diameter direction on the outer circumferential surface of the core part 200, and the stopper 230 may be formed in various shapes, but as illustrated, the stopper may protrude in the outer diameter direction from an upper end of an extending part extending from the lower side of the core part 200 to the upper side thereof, and a lower surface of the protruding portion may be formed to be inclined toward an outer upper side and an upper end surface thereof may be flat. As a result, the core part 200 may be easily inserted into the case 100, and may prevent the core part 200 from being released to the upper side, which is the direction opposite to the inserted direction. In addition, portions on which the stoppers 230 may be caught are formed in the case 100, and as illustrated, since the openings or the discharging port 120 formed in the side wall 102 of the case 100 are formed so that the stoppers 230 are caught on the upper ends thereof, there is an advantage that it is not necessary to form separate fixing grooves on which the stoppers 230 may be caught in the side wall 102.

In addition, the case 100 may have a first catching part 130 formed to protrude in the outer diameter direction on the upper end of the outer circumferential surface thereof, and a second catching part 150 formed to protrude in the outer diameter direction on the outer circumferential surface of the case 100 at a position spaced apart downwardly from the first catching part 130.

Figure 1:
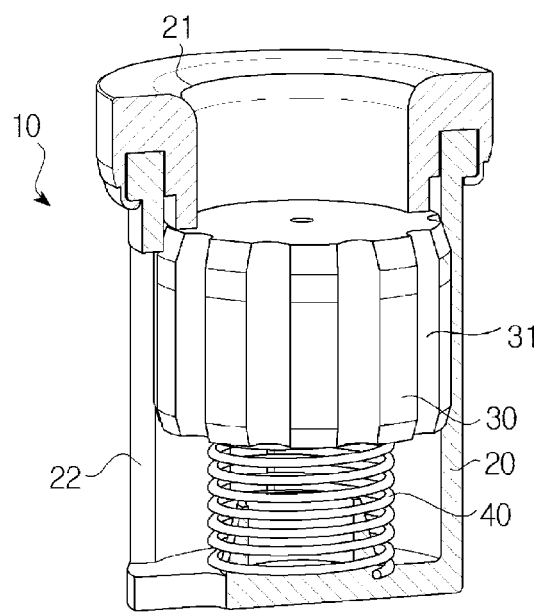
FIG. 1 is a cross-sectional view illustrating an apparatus for reducing suction pulsation of a conventional variable displacement swash plate type compressor.
Figure 2:
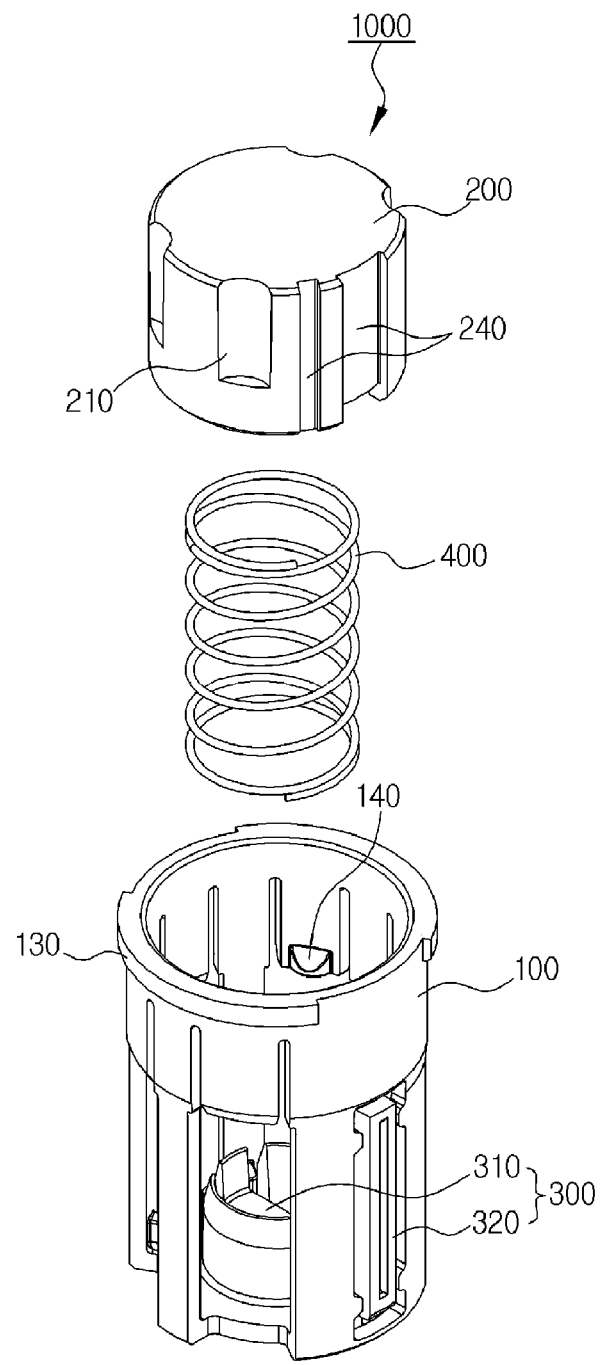
FIGS. 2 to 6 are an exploded perspective view, an assembled perspective view, and a cross-sectional view illustrating an apparatus for reducing suction pulsation according to a first exemplary embodiment of the present invention.
Figure 3:
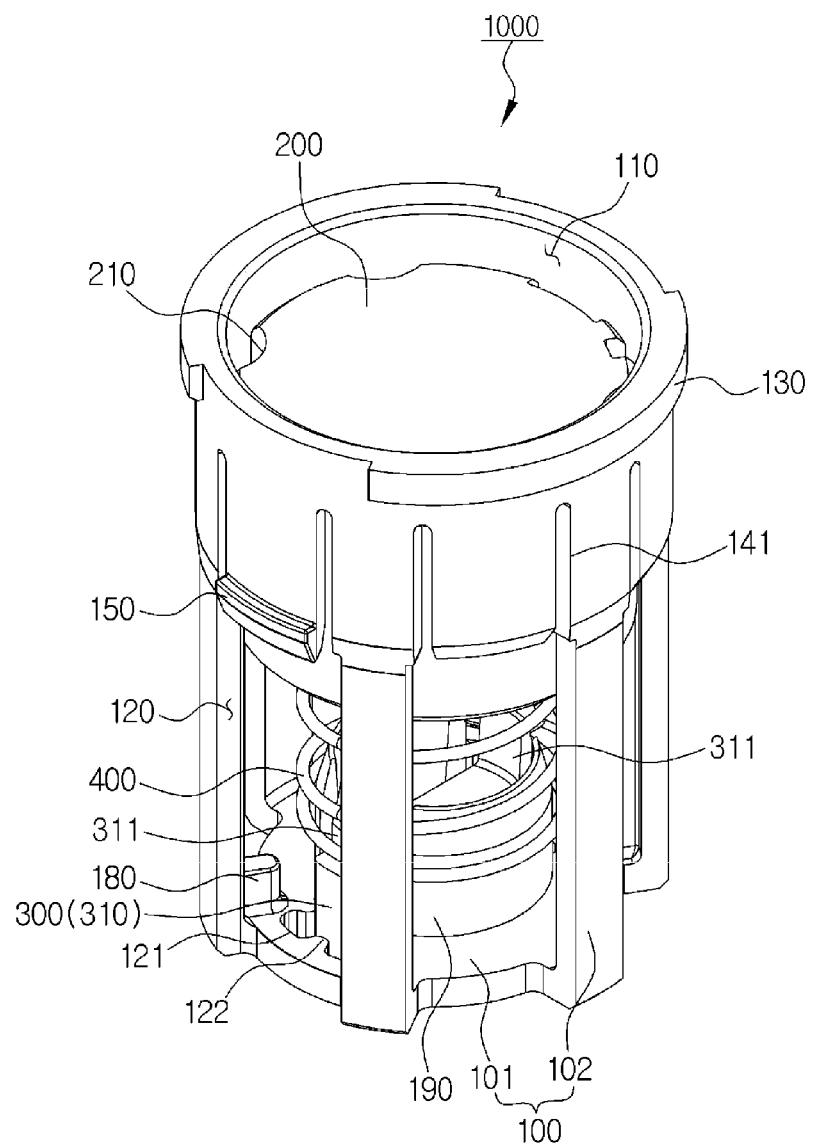
Figure 4:
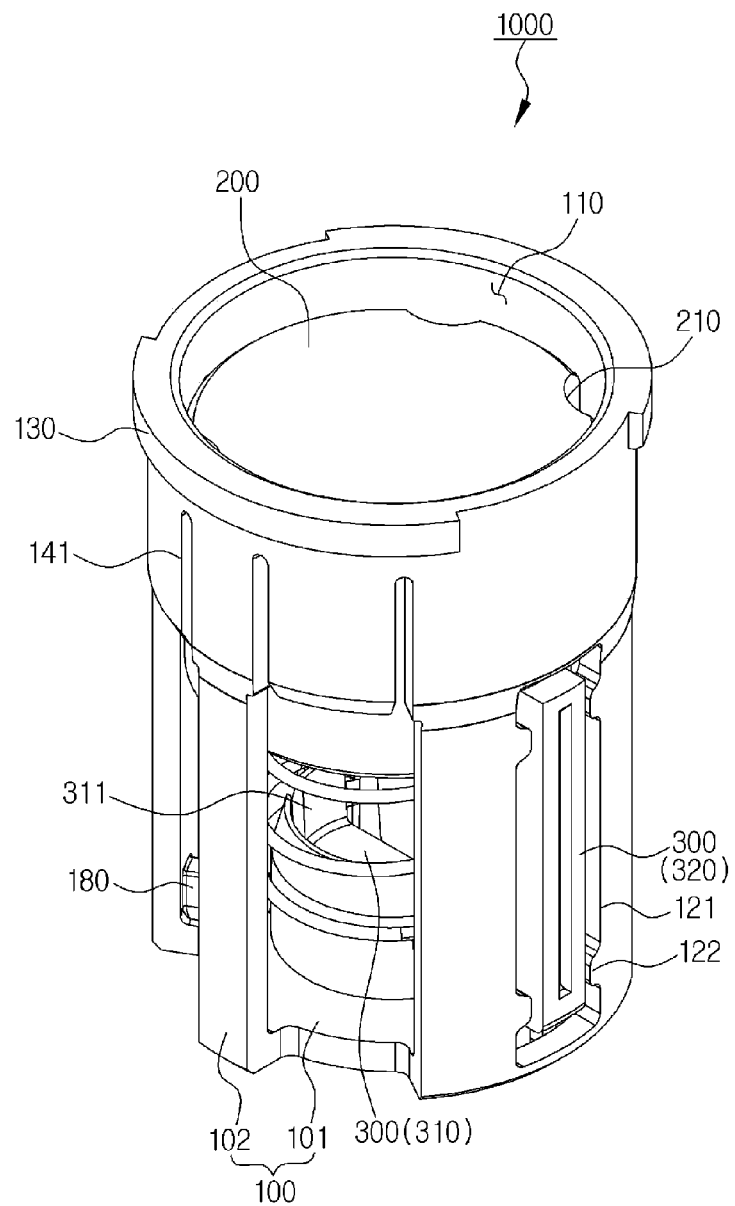
Figure 5:
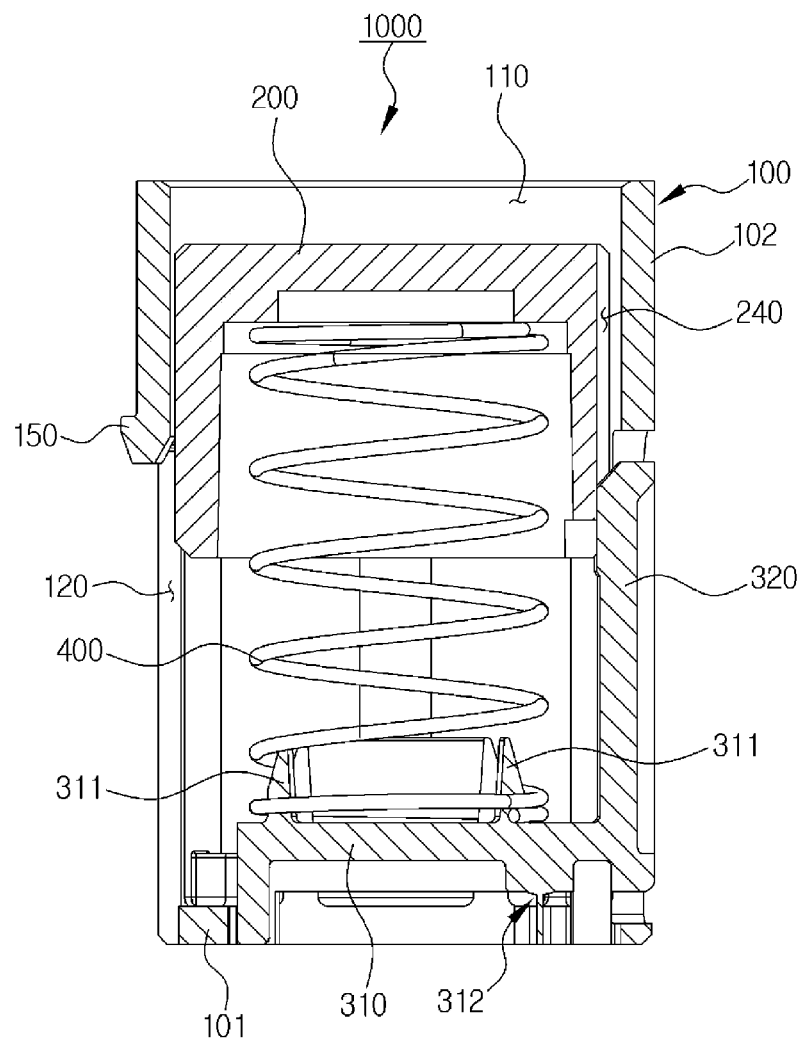
Figure 6:
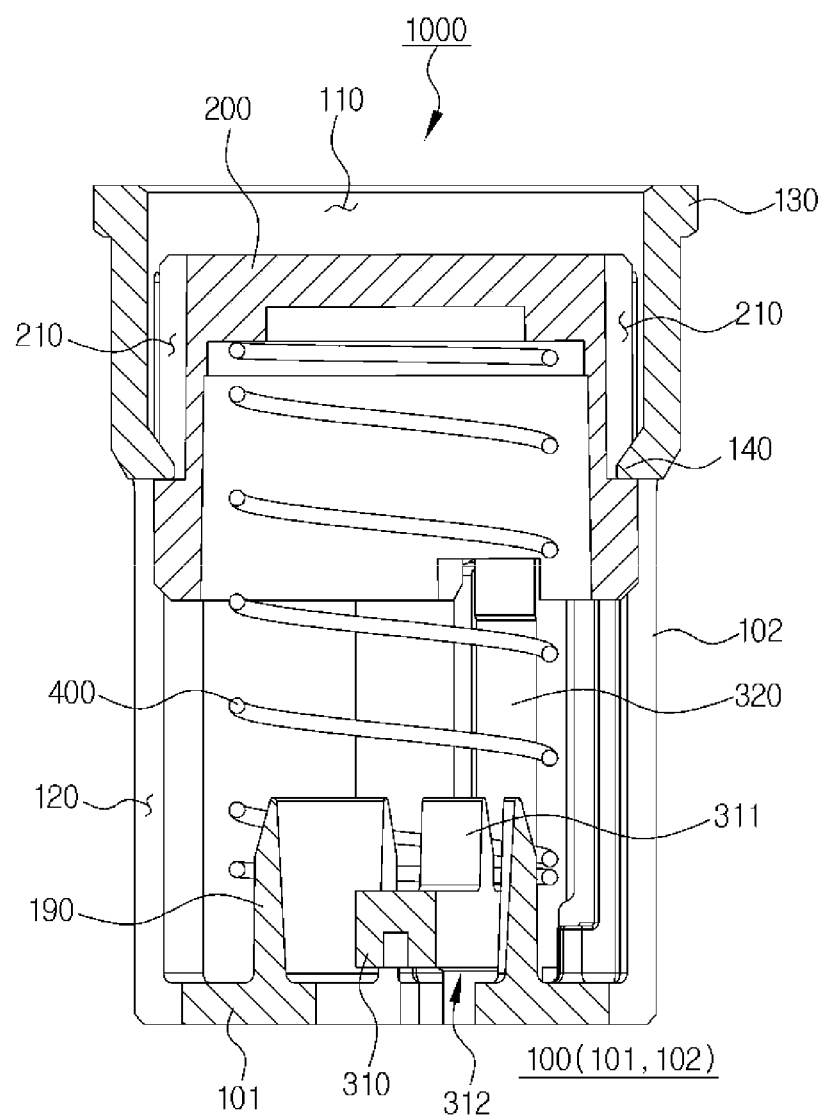

That is, since the case 100 is to be coupled to the rear housing 1100 of the swash plate type compressor and is to be firmly fixed thereto so as not to be separated from the rear housing 1100 of the swash plate type compressor, a structure in which a portion of the rear housing 1100 is sandwiched between the first catching part 130 and the second catching part 150 using the first catching part 130 formed on the case 100 and the second catching part 150 formed to be spaced apart from the first catching part 130 may be formed with reference to FIGS. 3 and 7. Here, the first catching part 130 may be formed in the form of a step protruding in the outer diameter direction from the upper end of the outer circumference of the case 100, and the first catching part 130 may have a ring shape formed over the entire circumferential direction, or may have the form in which a portion of the first catching part 130 in the ring shape has a groove in a vertical direction. The second catching part 150 may be formed to protrude in the outer diameter direction at the position spaced apart downwardly from the first catching part 130. In addition, the second catching part 150 may extend downwardly from the upper end of the opening or the discharging port 120 formed in the side wall 102, and may protrude in the outer diameter direction from the lower end portion of the extending part.

In addition, the case 100 may have a catching protrusion 161 protruding in the outer diameter direction from the upper end of the extending part 160 extended upwardly in the height direction from the upper end of the case 100.

That is, since the case 100 is to be coupled to the rear housing 1100 of the compressor and is to be firmly fixed thereto so as not to be separated from the rear housing 1100 of the compressor, the case 100 may be fixed to the rear housing 1100 using the catching protrusion 161 formed on the case 100. Here, the catching protrusion 161 may protrude more in the outer diameter direction than the outer circumference surface of the case 100, and the extending part 160 extends upwardly from the upper end of the side wall 102 so that the catching protrusion 161 may protrude from the upper end portion of the extending part 160.

Fifth Exemplary Embodiment

Figure 15:
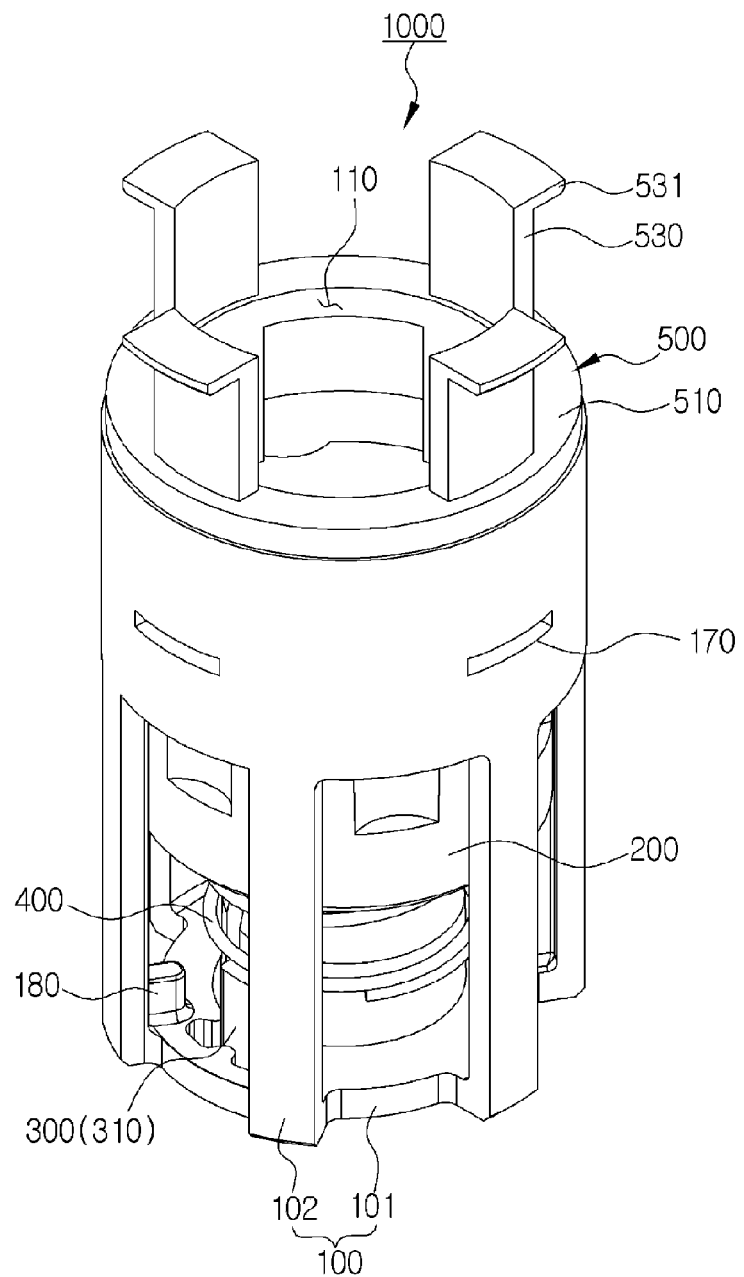
FIGS. 15 to 17 are an assembled perspective view, a cross-sectional view, and an exploded perspective view illustrating an apparatus for reducing suction pulsation according to a fifth exemplary embodiment of the present invention.
Figure 16:
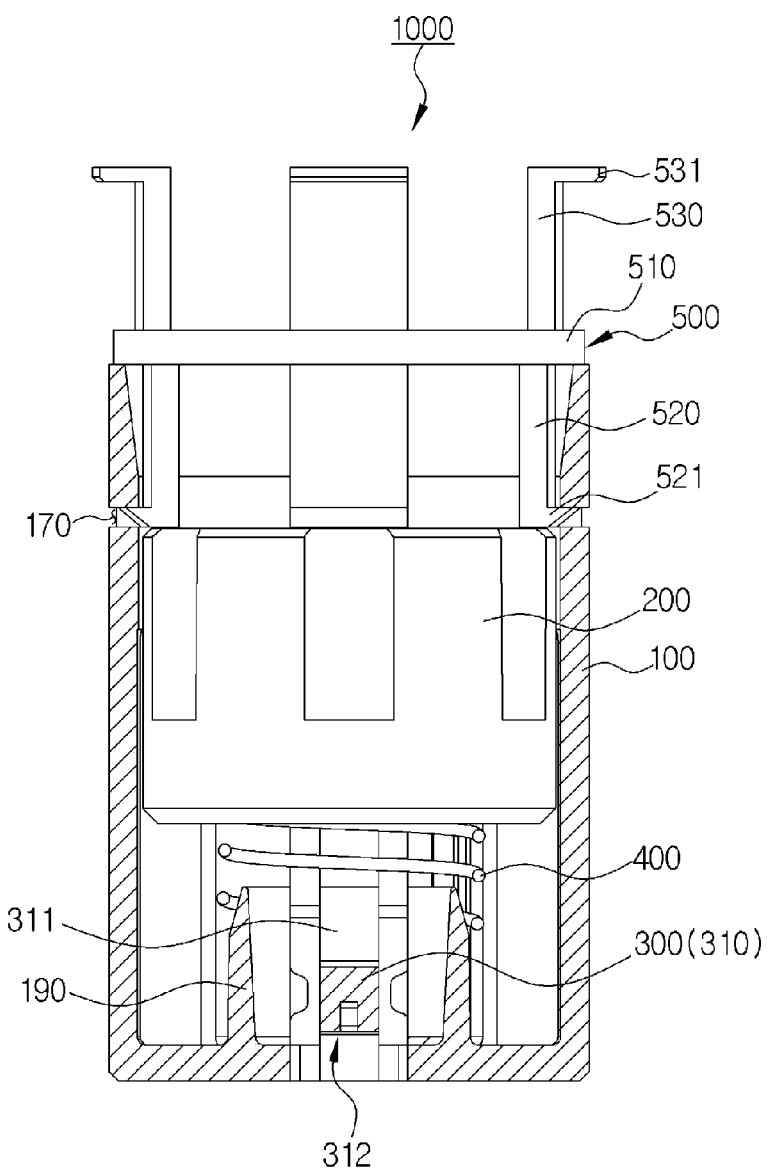
Figure 17:
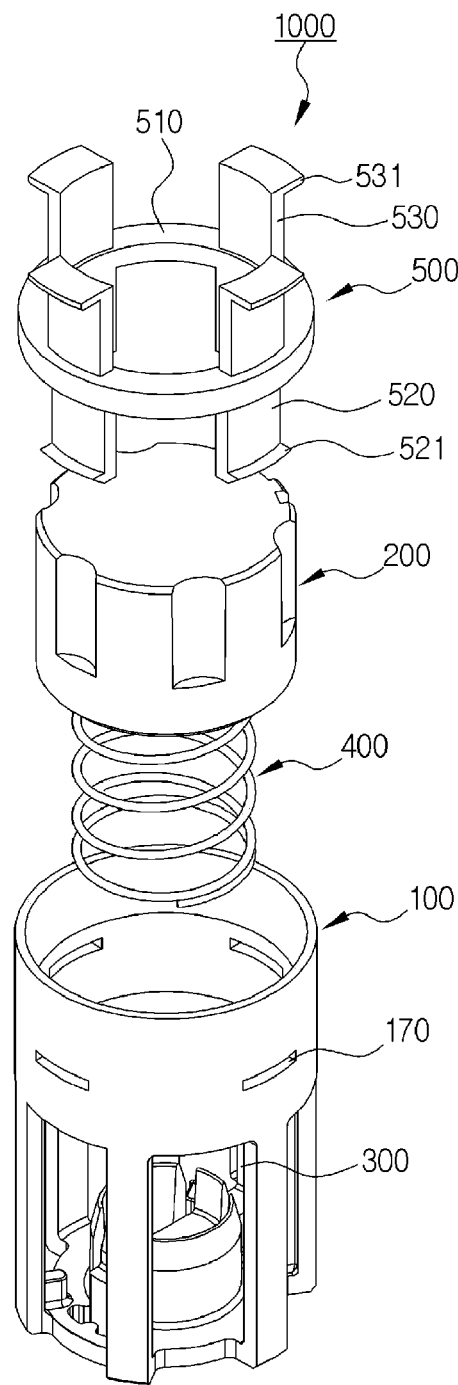

FIGS. 15 to 17 are an assembled perspective view, a cross-sectional view, and an exploded perspective view illustrating an apparatus for reducing suction pulsation according to a fifth exemplary embodiment of the present invention.

As illustrated, the apparatus for reducing suction pulsation further includes a fixing member 500 in which a plurality of extending parts 520 are extended downwardly from a ring part 510 to be spaced apart from each other in a circumferential direction so that coupling protrusions 521 protrude in the outer diameter direction from lower ends of the plurality of extending parts 520, and a plurality of extending parts 530 are extended upwardly from the ring part 510 to be spaced apart from each other in the circumferential direction so that catching protrusions 531 protrude in the outer diameter direction from upper ends of the plurality of extending parts 530, wherein the case 100 may have coupling grooves 170 formed therein so that the catching protrusions 531 of the fixing member 500 may be inserted and fixed to the coupling grooves 170 of the case 100.

This may prevent the core part 200 inserted into the case from being released to the outside of the case 100, and in addition, the apparatus for reducing suction pulsation further includes a separate fixing member 500, as a configuration capable of coupling and fixing the case 100 to the rear housing 1100 of the swash plate type compressor. That is, a lower side of the ring part 510 of the fixing member 500 is inserted into the case 100 so as to be coupled and fixed thereto, and as a result, the core part 200 may be caught on a lower end of the fixing member 500 so as not to release upwardly. Here, the fixing member 500 has the plurality of extending parts 520 formed downwardly from the ring part 510 formed in the ring shape, and the coupling protrusions 521 formed in the outer diameter direction from the lower end portions of the extending parts 520 may be inserted into coupling grooves 170 formed in the side wall 102 of the case 100 so as to be coupled and fixed to the coupling grooves 170. In addition, the fixing member 500 may be fixed to the rear housing 1100 of the swash plate type compressor using the plurality of extending parts 530 formed upwardly from the ring part 510 and the catching protrusions 531 protruding in the outer diameter direction from the upper end portions of the extending parts 530.

In addition, the case 100 may have a limiter 180 protruding inwardly from the bottom wall 101 or the side wall 102 to thereby limit a range in which the core part 200 may be moved downwardly.

That is, the limiter 180 may protrude upwardly from the upper surface of the bottom wall 101 or in the inner diameter direction from an inner side surface of the side wall 102, and when the core part 200 moves downwardly by a specific distance, the lower end of the core part 200 is supported on the limiter 180 so that it is possible to limit a lower limit position in a movement stroke of the core part 200.

In addition, the swash plate type compressor according to the present invention may include a rear housing 1100 in which a suction flow passage 1110 through which a refrigerant is introduced; and the apparatus 1000 for reducing suction pulsation insertedly installed on the suction flow passage of the rear housing 1100.

That is, the swash plate type compressor according to the present invention may have the apparatus 1000 for reducing suction pulsation insertedly installed on the suction flow passage through which the refrigerant is introduced. Here, as illustrated, a portion including the suction port 110 of the apparatus 1000 for reducing suction pulsation is positioned within the suction flow passage 1110 of the rear housing 1100 of the swash plate type compressor so that the suction port 110 may be installed to face an inlet side of the suction flow passage 1110 and the remaining portions including the discharging port 120 of the apparatus 1000 for reducing suction pulsation may be disposed to be positioned in a suction chamber 1140.

In addition, a catching jaw 1120 protrudes inwardly from the suction flow passage 1110 of the rear housing 1100, the case 100 has a first catching part 130 protruding in the outer diameter direction from the upper end of the outer circumferential surface thereof, and a second catching part 150 protruding in the outer diameter direction from the outer circumferential surface of the case 100 at a position spaced apart downwardly from the first catching part 130, and the catching jaw 1120 of the rear housing 1100 may be caught and sandwiched between the first catching part 130 and the second catching part 150 of the case 100.

That is, referring to FIG. 7, since the case 100 is to be coupled to the rear housing 1100 of the swash plate compressor and is to be firmly fixed thereto so as not to be separated from the rear housing 1100 of the swash plate compressor, the catching jaw 1120, which is a portion of the rear housing 1100, may be sandwiched between the first catching part 130 and the second catching part 150 using the first catching part 130 formed on the case 100 and the second catching part 150 formed to be spaced apart from the first catching part 130.

In addition, a catching groove 1130 is formed to be concave in the suction flow passage 1110 of the rear housing 1100, the case 100 has the catching protrusion 161 protruding in the outer diameter direction from the upper end of the extending part 160 extended upwardly in the height direction from the upper end of the case 100, and the catching protrusion 161 of the case 100 may be inserted and coupled to the catching groove 1130 of the rear housing 1100.

That is, since the case 100 is to be coupled to the rear housing 1100 of the compressor and is to be firmly fixed thereto so as not to be separated from the rear housing 1100 of the compressor, the case 100 may be fixed to the catching groove 1130 of the rear housing 1100 using the catching protrusion 161 formed on the case 100. Here, the catching groove 1130 may be formed to be concave in the inner circumferential surface of the suction flow passage 1110 of the rear housing 1100, and the catching groove 1130 is formed in a partial region along the circumferential direction and in a state in which the catching protrusion 161 of the case 100 is inserted and coupled to the catching groove 1130, the case 100 may be fixed so as not to be rotated in the circumferential direction.

In addition, a catching groove 1130 is formed to be concave in the suction flow passage 1110 of the rear housing 1100, and the apparatus 1000 for reducing suction pulsation further includes a fixing member 500 in which a plurality of extending parts 520 are extended downwardly from a ring part 510 to be spaced apart from each other in a circumferential direction so that coupling protrusions 521 protrude in the outer diameter direction from lower ends of the plurality of extending parts 520, and a plurality of extending parts 530 are extended upwardly from the ring part 510 to be spaced apart from each other in the circumferential direction so that catching protrusions 531 protrude in the outer diameter direction from upper ends of the plurality of extending parts 530, wherein the case 100 may have coupling grooves 170 formed therein so that the catching protrusions 521 of the fixing member 500 may be inserted and fixed to the coupling grooves 170 of the case 100, and the catching protrusions 531 of the case 100 may be inserted and coupled to the catching groove 1130 of the rear housing 1100.

Figure 18:
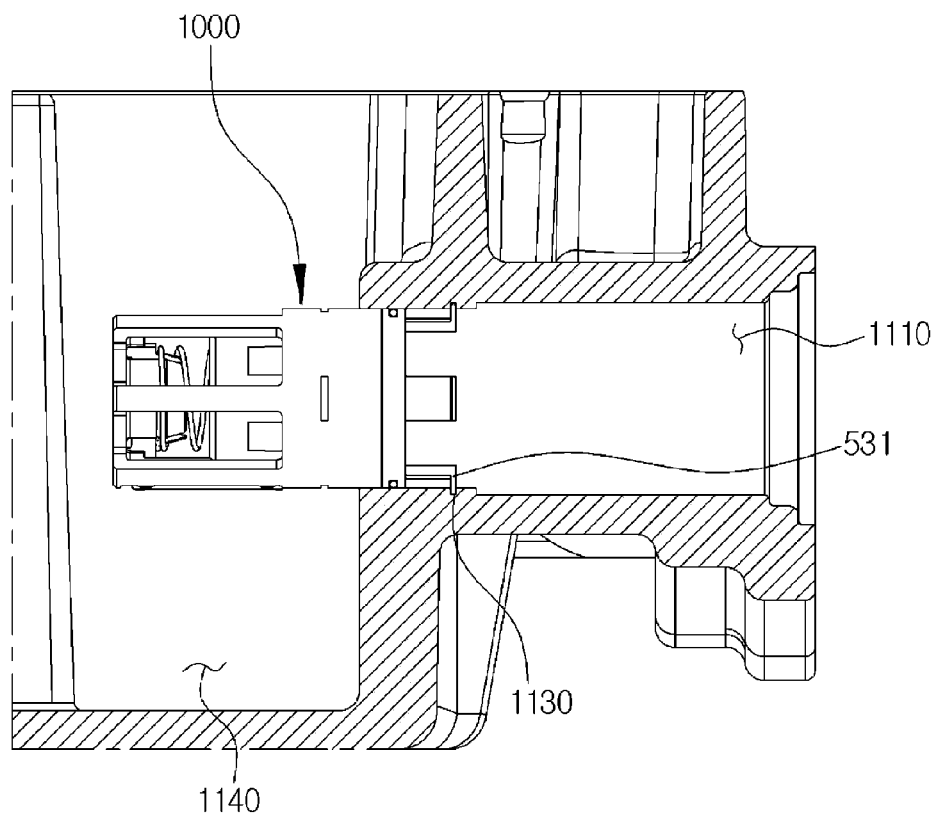
FIG. 18 is a cross-sectional view illustrating a state in which the apparatus for reducing suction pulsation according to a fifth exemplary embodiment of the present invention is installed and fixed onto a rear housing of a swash plate type compressor.

That is, when the apparatus 1000 for reducing suction pulsation further includes the fixing member 500 as described above, the catching protrusions 531 of the fixing member 500 may be inserted into the catching groove 1130 formed in the rear housing 1100 so as to be coupled and fixed thereto as illustrated in FIG. 18.

In addition, as illustrated in FIG. 19, a partial region of the catching jaw 1120 of the rear housing 1100 is formed as the hook coupling groove 1150 which is concave, and the second catching part 150 of the case 100 is coupled to the catching jaw 1120 so as to be caught on the catching jaw 1120 in a state in which it is seated in the hook coupling groove 1150, thereby making it possible to prevent the case 100 of the apparatus 1000 for reducing suction pulsation from being rotated.

The present invention is not limited to the abovementioned exemplary embodiments, but may be variously applied. In addition, the present invention may be variously modified by those skilled in the art to which the present invention pertains without departing from the gist of the present invention claimed in the claims.

DESCRIPTION OF REFERENCE NUMERALS

1000: apparatus for reducing suction pulsation
100: case 101: bottom wall 102: side wall
110: suction port 120: discharging port 121: opening
122: protrusion 130: first catching part 140: core hook part
141: slit 150: second catching part 160: extending part
161: catching protrusion 170: coupling groove 180: limiter
190: fitting part 200: core part 210: hook moving groove
220: blocking wall 230: stopper 240: guide groove
300: lever 310: horizontal part 311: fitting part
312: coupling part 320: vertical part 400: elastic means
500: fixing member 510: ring part 520 extending part
521: coupling protrusion 530: extending part 531: catching protrusion
1100: rear housing 1110: suction flow passage
1120: catching jaw 1130: catching groove
1140: suction chamber 1150: hook coupling groove

The invention claimed is:

1. An apparatus reducing suction pulsation comprising:
a case having a suction port having an upper side surface opened in a height direction and a discharging port formed by hollowing a predetermined region of a side wall;
  a core part provided between the suction port and the discharging port in the case to be movable in the height direction, and disposed to be spaced apart from a bottom surface of the case;
  a lever in which a vertical part extends upwardly along the side wall of the case at one end of a horizontal part disposed in the vicinity of the bottom wall of the case to dispose an upper side of the vertical part adjacent an outer circumferential surface of the core part, and a portion at which the horizontal part and the vertical part meet is rotatably coupled to the case about a horizontal shaft; and
  an elastic material interposed between the core part and the horizontal part of the lever and having an upper end supported by the core part and a lower end supported by the horizontal part.

2. The apparatus for reducing suction pulsation of claim 1, wherein the case and the lever are integrally formed of a plastic material by injection.

3. The apparatus for reducing suction pulsation of claim 1, wherein the lever is disposed in an opening formed in the bottom wall and the side wall so as to penetrate through an inner side and an outer side of the case.

4. The apparatus for reducing suction pulsation of claim 3, wherein protrusions protrude toward the lever so as to be adjacent the lever on a circumferential surface forming the opening.

5. The apparatus for reducing suction pulsation of claim 1, wherein an upper surface of the horizontal part of the lever is positioned above an upper surface of the bottom wall of the case, and
  a lower end of the elastic material is supported by the horizontal part, and the lower end of the elastic material is disposed spaced apart from an upper side of the bottom wall.

6. The apparatus for reducing suction pulsation of claim 1, wherein a core hook part protrudes in an inner diameter direction on a predetermined region of an inner circumferential surface of the case so that the core part is caught on the core hook part in a state in which the core part is inserted into the case and does not escape upwardly.

7. The apparatus for reducing suction pulsation of claim 6, wherein a hook moving groove is formed in the outer circumferential surface of the core part at a position corresponding to the core hook part so as to be concave from the upper end of the core part to a height spaced apart upwardly from the lower end thereof, and the core hook part is inserted into the hook moving groove.

8. The apparatus for reducing suction pulsation of claim 1, wherein slits cut in the height direction at both ends in the circumferential direction in which the core hook part is formed are formed in the case.

9. The apparatus for reducing suction pulsation of claim 8, wherein the core part has a plurality of blocking walls extended upwardly from the upper surface of the core part of positions corresponding to positions at which the slits are formed.

10. The apparatus for reducing suction pulsation of claim 1, wherein stoppers protrude in the outer diameter direction on a predetermined region of the outer circumferential surface of the core part, and the stoppers are caught on an upper end of the opening formed to penetrate through the side wall of the case in a state in which the core part is inserted into the case to prevent the core part from escaping upwardly.

11. The apparatus for reducing suction pulsation of claim 1, wherein the case has a first catching part formed to protrude in the outer diameter direction on the upper end of the outer circumferential surface thereof, and a second catching part formed to protrude in the outer diameter direction on the outer circumferential surface of the case at a position spaced apart downwardly from the first catching part.

12. The apparatus for reducing suction pulsation of claim 1, wherein the case has a catching protrusion protruding in the outer diameter direction from an upper end of an extending part extended upwardly in the height direction from the upper end of the case.

13. The apparatus for reducing suction pulsation of claim 1, further comprising: a fixing member in which a plurality of extending parts are extended downwardly from a ring part to be spaced apart from each other in a circumferential direction so that coupling protrusions protrude in the outer diameter direction from lower ends of the plurality of extending parts, and a plurality of extending parts are extended upwardly from the ring part to be spaced apart from each other in the circumferential direction so that catching protrusions protrude in the outer diameter direction from upper ends of the plurality of extending parts,
  wherein the case has coupling grooves formed therein so that the catching protrusions the coupling protrusions of the fixing member are inserted and fixed to the coupling grooves of the case.

14. The apparatus for reducing suction pulsation of claim 1, wherein the case has a limiter protruding inwardly from the bottom wall or the side wall to limit a range in which the core part is moved downwardly.

15. A swash plate type compressor comprising:
  a rear housing in which a suction flow passage through which a refrigerant is introduced; and
  the apparatus for reducing suction pulsation of claim 1 insertedly installed on the suction flow passage of the rear housing.

16. The swash plate type compressor of claim 15, wherein a catching jaw protrudes inwardly from the suction flow passage of the rear housing, the case has a first catching part protruding in the outer diameter direction from the upper end of the outer circumferential surface thereof, and a second catching part protruding in the outer diameter direction from the outer circumferential surface of the case at a position spaced apart downwardly from the first catching part, and the catching jaw of the rear housing is caught and sandwiched between the first catching part and the second catching part of the case.

17. The swash plate type compressor of claim 16, wherein a catching groove is formed to be concave in the suction flow passage of the rear housing, the case has catching protrusion protruding in the outer diameter direction from an upper end of an extending part extended upwardly in the height direction from the upper end of the case, and the catching protrusion of the case is inserted and coupled to the catching groove of the rear housing.

18. The swash plate type compressor of claim 15, wherein a catching groove is formed to be concave in the suction flow passage of the rear housing, and the apparatus for reducing suction pulsation further includes a fixing member in which a plurality of extending parts are extended downwardly from a ring part to be spaced apart from each other in a circumferential direction so that coupling protrusions protrude in the outer diameter direction from lower ends of the plurality of extending parts, and a plurality of extending parts are extended upwardly from the ring part to be spaced apart from each other in the circumferential direction so that catching protrusions protrude in the outer diameter direction from upper ends of the plurality of extending parts, wherein the case has coupling grooves formed therein so that the catching protrusions of the fixing member are inserted and fixed to the coupling grooves of the case, and the catching protrusions of the case are inserted and coupled to the catching groove of the rear housing.

* * * * *